(12) United States Patent
Kondo

(10) Patent No.: US 8,980,627 B2
(45) Date of Patent: Mar. 17, 2015

(54) METHOD FOR ENABLING STABLE EXPRESSION OF TRANSGENE

(75) Inventor: Takashi Kondo, Saitama (JP)

(73) Assignee: Riken, Saitama (JP)

(*) Notice: Subject to any disclaimer, the term of this patent is extended or adjusted under 35 U.S.C. 154(b) by 709 days.

(21) Appl. No.: 12/515,584

(22) PCT Filed: Nov. 21, 2007

(86) PCT No.: PCT/JP2007/073003
§ 371 (c)(1),
(2), (4) Date: May 20, 2009

(87) PCT Pub. No.: WO2008/062904
PCT Pub. Date: May 29, 2008

(65) Prior Publication Data
US 2010/0205683 A1    Aug. 12, 2010

(30) Foreign Application Priority Data
Nov. 21, 2006  (JP) .................. 2006-314307

(51) Int. Cl.
| | | |
|---|---|---|
| *C12N 15/00* | (2006.01) | |
| *C12N 5/00* | (2006.01) | |
| *C12N 5/02* | (2006.01) | |
| *C12P 21/06* | (2006.01) | |
| *C07H 21/04* | (2006.01) | |
| *A01K 67/027* | (2006.01) | |
| *C07K 14/47* | (2006.01) | |
| *C12N 15/85* | (2006.01) | |

(52) U.S. Cl.
CPC ......... *A01K 67/0275* (2013.01); *C07K 14/4705* (2013.01); *C12N 15/8509* (2013.01); *A01K 2217/052* (2013.01); *A01K 2217/072* (2013.01); *A01K 2227/105* (2013.01); *A01K 2267/03* (2013.01); *A01K 2267/0393* (2013.01); *C12N 2830/40* (2013.01)
USPC ....... 435/325; 435/320.1; 435/455; 435/69.1; 536/23.5

(58) Field of Classification Search
CPC .............. A01K 67/0275; A01K 2217/052; A01K 2217/072; A01K 2227/105; C07K 14/4705; C12N 15/8509; C12N 2830/40
USPC .............. 435/320.1, 325, 349, 455, 69.1; 536/23.5
See application file for complete search history.

(56) References Cited

FOREIGN PATENT DOCUMENTS

| JP | 10-191975 | 7/1998 |
|---|---|---|
| JP | 2000-228925 | 8/2000 |
| WO | WO-2005/098041 | 10/2005 |

OTHER PUBLICATIONS

Clark et al. Nature Reviews: 4: 825-833, 2003.*
Kondo et al. Cell, 97: 407-417, 1999.*
Clone RP23-400H17, submitted Dec. 12, 2001, Whitehead Institute.*
International Search Report PCT/JP2007/073003 dated Dec. 25, 2007.
Takumi Yamagishi et al., "Evx2-Hoxd13 Intergenic Region Restricts Enhancer Association to Hoxd13 Promoter", PLoS ONE, Issue 1, Jan. 2007, e175, pp. 1-8.
DatabaseDDBJ/EMBL/GenBank [online], Accession No. AB032481, http://www.ncbi.nlm.nih.gov/entrez/viewer.fcgi?db=nuccore&id=7707676 retrieval date Dec. 13, 2007 submitted Sep. 17, 1999, Y. Arai et al., Definition *Homo sapiens* HOXD13 gene for homeobox transcription factor, complete cds.
Akiko Nagai et al., "Analysis of chromosomal boundary region located between Hoxd13 and Evx2", Abstracts of the Annual Meeting for the Japanese Society of Development Biologists Taikai Happyo Yoshishu, 37th, p. 190, 2P047 (2004).
Francois Spitz et al., "A Global Control Region Defines a Chromosomal Regulatory Landscape Containing the HoxD Cluster", Cell, vol. 113, 405-417, May 2, 2003.
Ignacio Monge et al., "An enhancer-titration effect induces digit-specific regulatory alleles of the HoxD cluster", Developmental Biology 256 (2003) 212-220.
Adam G. West et al., "Insulators: many functions, many mechanisms", Genes & Development 16:271-288, 2002.
Maria Kmita et al., "Evolutionary conserved sequences are required for the insulation of the vertebrate Hoxd complex in neural cells", Development, 129, 5521-5528, 2002.
Marie Kmita et al., "Targeted inversion of a polar silencer within the HoxD complex re-allocates domains of enhancer sharing", Nature Genetics, vol. 26, Dec. 2000, pp. 451-454.
Dasari Vasanthi et al., "A functionally conserved boundary element from the mouse HoxD locus requires GAGA factor in *Drosophila*", Development 137, 4239-4247, 2010.
Pascal Dolle et al., "Developmental expression of the mouse Evx-2 gene: relationship with the evolution of the HOM-Hox complex", Development 1994 Supplement, 143-153, 1994.
Supplementary European Search Report EP 07 83 2718 dated Oct. 25, 2011.

(Continued)

Primary Examiner — Thaian N Ton
(74) Attorney, Agent, or Firm — Foley & Lardner LLP

(57) ABSTRACT

This invention relates to a method for stably expressing a transgene integrated into the genome of an animal cell or of an animal over a long period. Specifically, this invention provides: an approximately 2.5 kb XhoI-BamHI fragment (or XB fragment) derived from the Evx2-Hoxd13 intergenic region of the animal genome, or a homologue thereof; a DNA containing a foreign DNA wherein the DNA has been inserted between the two essentially identical XB fragments or homologues thereof; a vector, animal cell, or nonhuman mammalian animal containing said DNA; and use of the vector, animal cell, or nonhuman mammalian animal for production of a substance or therapy.

7 Claims, 7 Drawing Sheets
(5 of 7 Drawing Sheet(s) Filed in Color)

(56) References Cited

OTHER PUBLICATIONS

Yann Herault et al., "A nested deletion approach to generate Cre deleter mice with progressive Hox profiles", Int. J. Dev. Biol. 46: 185-191, 2002.

Yann Herault et al., "Function of the Evx-2 gene in the morphogenesis of vertebrate limbs", The EMBO Journal, vol. 15, No. 23, pp. 6727-6738, 1996.

* cited by examiner

Fig. 4
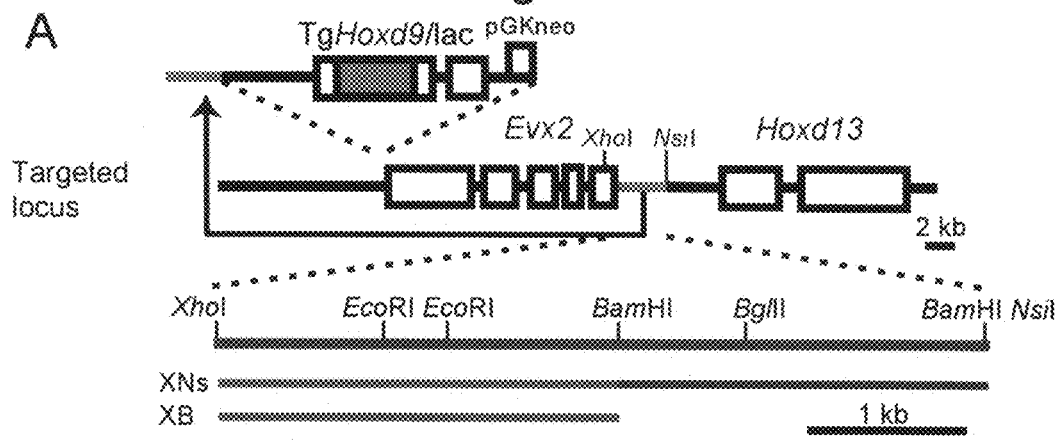
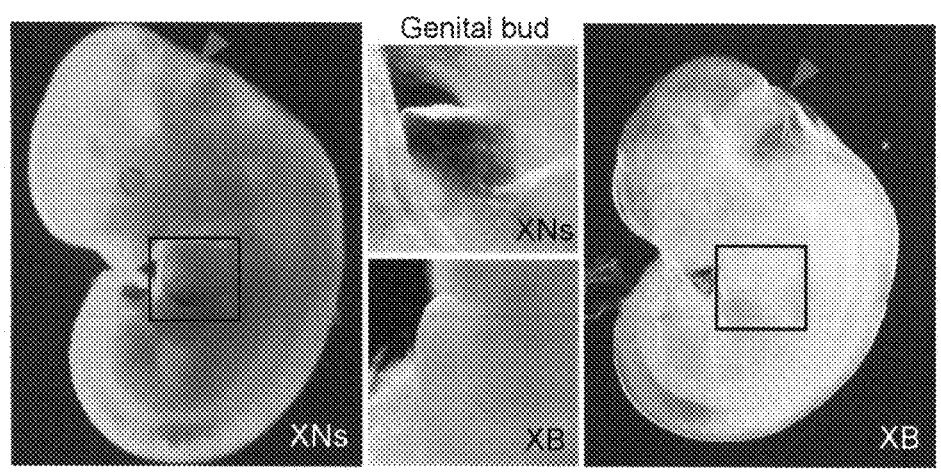
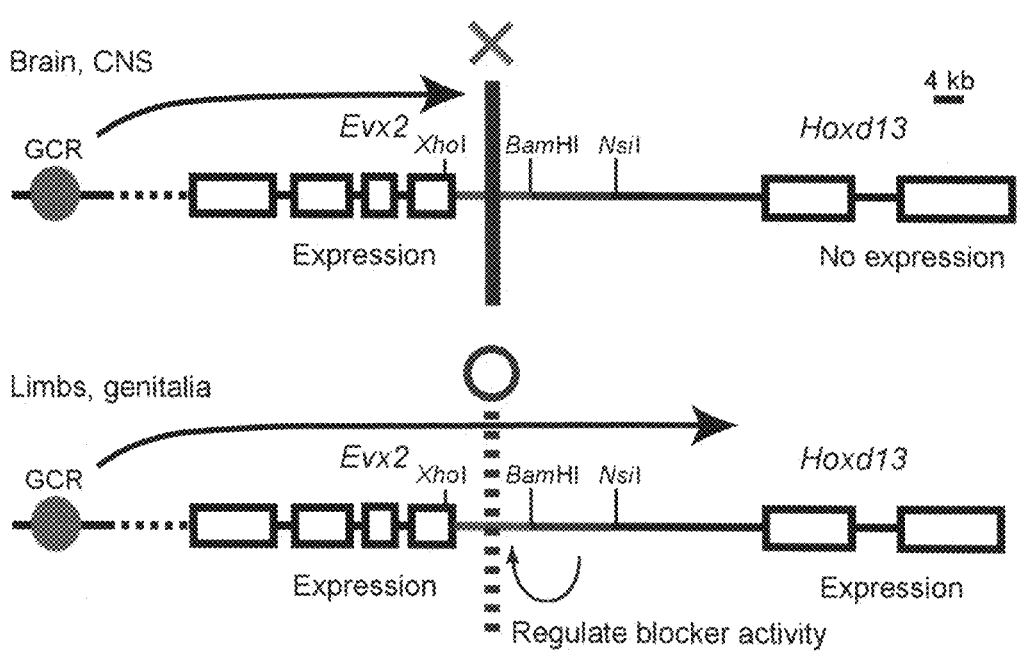

Fig. 5
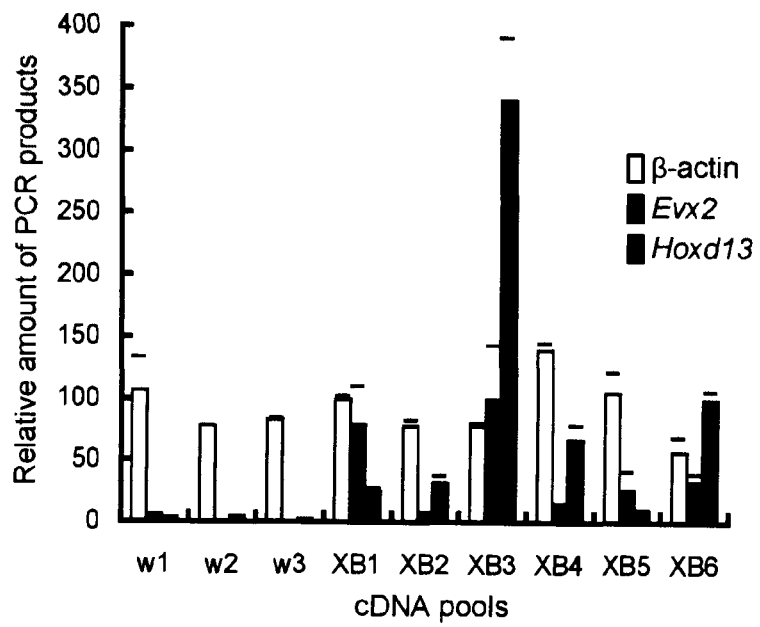
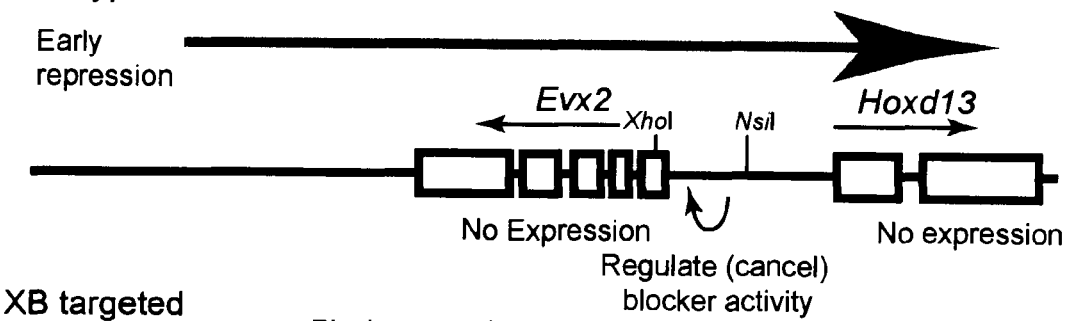
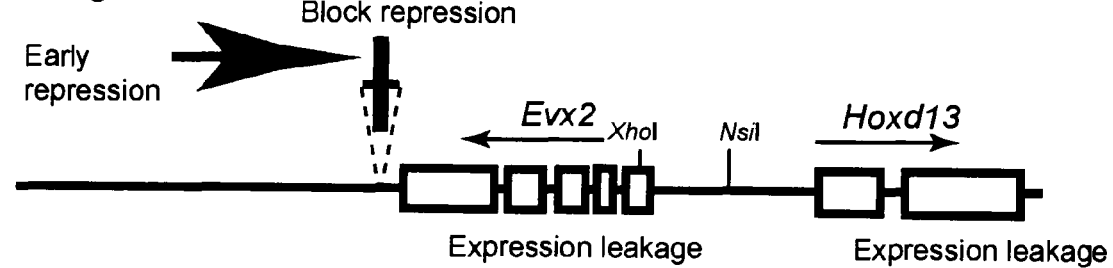

Fig. 6
A
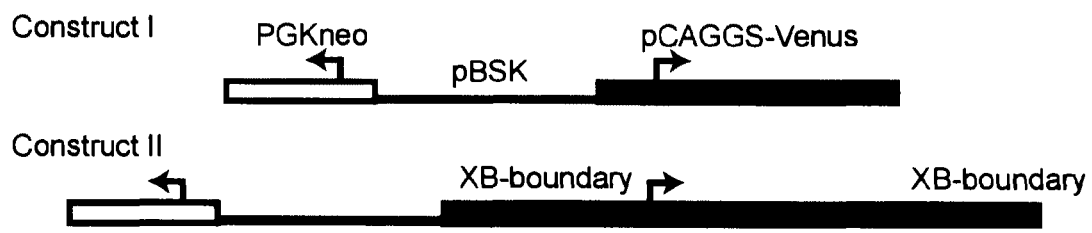
B
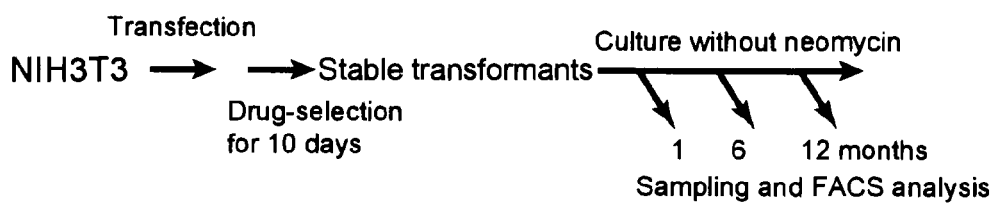
C
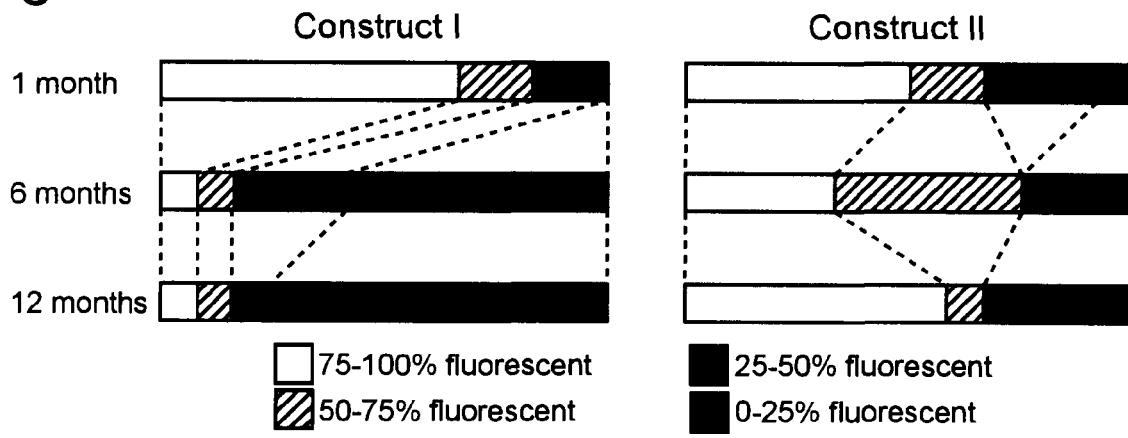

METHOD FOR ENABLING STABLE EXPRESSION OF TRANSGENE

CROSS-REFERENCE TO RELATED PATENT APPLICATIONS

This application is the U.S. National Stage of PCT/JP2007/073003 filed Nov. 21, 2007, which claims priority from Japanese Application No. 2006-314307 filed Nov. 21, 2006, each of which is incorporated herein by reference in its entirety.

SEQUENCE LISTING

The instant application contains a Sequence Listing which has been submitted via EFS-Web and is hereby incorporated by reference in its entirety. Said ASCII copy, created on Dec. 23, 2009, is named 81356329.txt, and is 12,079 bytes in size.

TECHNICAL FIELD

The present invention relates to a method for enabling stable expression of a transgene for a long period of time by utilizing a certain DNA fragment, or a homolog thereof, from the Evx2-Hoxd13 intergenic region of an animal genome.

The present invention also relates to an animal cell, or a transgenic nonhuman mammalian animal, which expresses a foreign DNA contained in such transgene and which enables long-term stable production of a (poly)peptide or protein encoded by the foreign DNA.

The present invention further relates to the DNA fragment or homologue thereof, to a DNA containing a foreign DNA, wherein the DNA has been inserted between the two DNA fragments or homologues thereof, and to a vector comprising said DNA.

BACKGROUND ART

Proteins-DNA interaction on DNA cis-regulatory elements and further cross-talk among protein-DNA complexes decide precise transcription regulation. Since genes are embedded in huge DNA molecules, i.e., chromosomes of higher eukaryotes, which contain abundant of putative cis-regulatory elements such as enhancer and promoter sequences, this interaction of cis-regulatory sequences required for precise regulation of gene expression is extremely complicated. In order to achieve proper transcription regulation, selection of these interactions will be inevitable. Some of the DNA regions are believed to have roles for such traffic controls for these interactions among cis-regulatory elements.

Boundary elements divide a chromosome into units which are independent each other for transcription regulation. Several candidates for boundary elements were isolated mainly from genetic study of Drosophila melanogaster (M. Peifer and W. Bender, EMBO J. 1986, 5: 2293-2303; H. Gyurkovics et al., EMBO J. 1990, 9: 2579-2585; R. Kellum and P. Schedl, Mol. Cell. Biol. 1992, 12: 2424-2431; Georgiev and Corces, Proc. Natl. Acad. Sci. U.S.A., 1995, 92: 5184-5188; S. Barges et al., Development 2000, 127:779-790). Many of them are involved in the cis-regulatory elements for homeotic gene regulation (M. Peifer and W. Bender, EMBO J. 1986, 5: 2293-2303; H. Gyurkovics et al., EMBO J. 1990, 9: 2579-2585; S. Barges et al., Development 2000, 127:779-790). Use of an enhancer must be well organized to achieve proper transcription regulation of clustered homeotic genes to construct proper anterior-posterior segmental identity within an animal body. Mutations in these sequences give alterations in expression profiles of the genes and morphological shift of segmental identities (H. Gyurkovics et al., EMBO J. 1990, 9: 2579-2585; J. Mihaly et al., Development 1997, 124: 1809-1820).

Similar phenomenon has been observed also in mammalian orthologous homeotic genes (T. Kondo et al., Mol. Cell. 1998, 1: 289-300; M. Kmita et al., Nat. Genet. 2000, 26: 451-454). Homeobox Hox genes are responsible for anterior-posterior identity of the mammalian body as shown in *Drosophila*. Mis-regulation of Hox genes causes morphological alterations (T. Akasaka et al., Development 1996, 122: 1513-1522; N. Core et al., Development 2000, 124: 721-729) and can even be detrimental in some cases (T. Kondo and D. Duboule, Cell 1999, 97: 407-417; M. Kmita et al., Development 2002, 129: 5521-5528). As in the case of fruit fly, the enhancer-promoter interactions need to be organized for the Hox gene expression regulation (T. Kondo et al., Mol. Cell. 1998, 1: 289-300; M. Kmita et al., Nat. Genet. 2000, 26: 451-454). An enhancer that regulates the expression of Hoxd11 gene in cecum cannot associate to the promoter of Hoxd13 which is about 10 kb of distance from Hoxd11, whereas in mice with Hoxd12-Hoxd13 intergenic deletion the Hoxd13 gene gives its expression in cecum resembling Hoxd11 (T. Kondo et al., Mol. Cell. 1998, 1: 289-300; M. Kmita et al., Nat. Genet. 2000, 26: 451-454). Thus, it was concluded that Hoxd12-Hoxd13 intergenic sequence functions as an insulator.

Since the boundary element is expected to divide a chromosome into multiple units, enhancer activity cannot reach the promoter beyond the boundary sequence (which is called insulator activity). However, the enhancer insulation activity is only one aspect of boundary element. Addition to this, a boundary element also prevents the spreading of the heterochromatin which represses the expression of genes (J. Mihaly et al., Development 1997, 124: 1809-1820). Recently it is found that these two activities, insulation activity and position effect protection activity, can be separable from each other (F. Recillas-Targa et al., Proc. Natl. Acad. Sci. U.S.A., 2002, 99: 6883-6888).

DISCLOSURE OF THE INVENTION

The present inventors have now found a novel candidate for the boundary element within the HoxD complex (i.e., the Evx2-Hoxd13 intergenic region). The present inventors have also now found that such fragment actually has an insulation activity and a positional value protecting activity, that the boundary sequence functions in a tissue-specific manner, and that such tissue-specific regulation can be separated from boundary activity. As a result of evolutionary research based on such findings, the present inventors have now found that a new transgene, which is prepared by inserting a foreign DNA into a region between the two identical boundary fragments, can be stably expressed in an animal cell for a long period of time.

Accordingly, an object of the present invention is to provide a method for stably expressing said transgene in a cell or animal, and an animal cell or nonhuman mammalian animal that enables such expression.

The present invention has the following features.

(1) A transformed animal cell comprising, on the genome, a DNA containing a foreign DNA, wherein the DNA has been inserted between two essentially identical XhoI-BamHI fragments (or XB fragments) of each approximately 2.5 kb from the Evx2-Hoxd13 intergenic region of the animal genome, or between two essentially identical homologues of the XB fragments having a biological function equivalent to that thereof.

(2) The transformed animal cell according to (1), wherein the animal cell is a differentiated cell.

(3) The transformed animal cell according to (1) or (2), wherein the animal cell is a vertebrate cell.

(4) The transformed animal cell according to (3), wherein the vertebrate cell is a mammalian cell or avian cell.

(5) The transformed animal cell according to any one of (1) to (4), wherein the XB fragment comprises a nucleotide sequence as shown in SEQ ID NO: 1, SEQ ID NO: 2, or SEQ ID NO: 3, or a nucleotide sequence having at least 99% identity to the nucleotide sequence.

(6) The transformed animal cell according to any of (1) to (5), wherein the foreign DNA encodes a peptide, polypeptide, or protein.

(7) A transgenic nonhuman mammalian animal comprising, on the genome, a DNA containing a foreign DNA, wherein the DNA has been inserted between two essentially identical XhoI-BamHI fragments (or XB fragments) of each approximately 2.5 kb from the Evx2-Hoxd13 intergenic region of the nonhuman mammalian animal genome, or between two essentially identical homologues of the XB fragments having a biological function equivalent to that thereof.

(8) The transgenic nonhuman mammalian animal according to (7), which is a mouse.

(9) The transgenic nonhuman mammalian animal according to (7) or (8), wherein the XB fragment comprises the nucleotide sequence as shown in SEQ ID NO: 1 or a nucleotide sequence having at least 99% identity to said nucleotide sequence.

(10) The transgenic nonhuman mammalian animal according to any of (7) to (9), wherein the foreign DNA encodes a peptide, polypeptide, or protein.

(11) A method for producing the transformed animal cell according to any one of (1) to (6) comprising the following steps of:

preparing two essentially identical XhoI-BamHI fragments (or XB fragments) of each approximately 2.5 kb from the Evx2-Hoxd13 intergenic region in the animal cell genome, or two essentially identical homologues of the XB fragments having a biological function equivalent to that thereof;

forming a foreign DNA-containing DNA, which has been inserted between the XB fragments or homologues thereof or flanked by them;

inserting the obtained DNA into a vector; and introducing the vector into an animal cell to integrate the DNA into the genome of the cell, thereby obtaining the transformed animal cell.

(12) The method according to (H), wherein the DNA is integrated into the genome of the cell by homologous recombination.

(13) The method according to (11), wherein the DNA is integrated into the genome of the cell at random.

(14) The method according to any of (11) to (13), wherein the vector further comprises a selection marker.

(15) A method for producing the transgenic nonhuman mammalian animal according to any one of (7) to (10) comprising the following steps of:

preparing a foreign DNA-containing DNA, which has been inserted between two essentially identical XhoI-BamHI fragments (or XB fragments) of each approximately 2.5 kb from the Evx2-Hoxd13 intergenic region of the animal cell genome or two essentially identical homologues of the XB fragments having a biological function equivalent to that thereof, or which has been flanked by the XB fragments or homologues thereof, followed by inserting the DNA into a vector;

introducing the obtained vector into an egg cell or embryonic stem (ES) cell derived from the nonhuman animal;

transplanting the egg cell or ES cell to a surrogate female parent animal; and obtaining a chimeric animal comprising the foreign DNA via childbirth.

(16) The method according to (15), wherein the nonhuman mammalian animal is a mouse.

(17) The method according to (15), wherein the nonhuman mammalian animal is an ungulate.

(18) The method according to any one of (15) to (17), which further comprises crossing between the chimeric animals or between the chimeric animal and the wild-type animal to produce homozygous offspring.

(19) An approximately 2.5 kb XhoI-BamHI fragment (or XB fragment) derived from the Evx2-Hoxd13 intergenic region of an animal genome, or a homologue thereof.

(20) A DNA containing a foreign DNA, wherein the DNA has been inserted between two essentially identical XhoI-BamHI fragments (or XB fragments) of each approximately 2.5 kb from the Evx2-Hoxd13 intergenic region of an animal genome, or between two essentially identical homologues of the XB fragments having a biological function equivalent to that thereof.

(21) A DNA containing a foreign DNA, wherein the DNA has been flanked by XhoI-BamHI fragments (or XB fragments) of each approximately 2.5 kb from the Evx2-Hoxd13 intergenic region of an animal genome or by homologues of the XB fragments having a biological function equivalent to that thereof

(22) The DNA according to (20) or (21), wherein the animal is a vertebrate.

(23) The DNA according to (22), wherein the vertebrate is a mammalian animal or avian.

(24) The DNA according to any one of (20) to (23), wherein the XB fragment comprises a nucleotide sequence as shown in SEQ ID NO: 1, SEQ ID NO: 2, or SEQ ID NO: 3 or a nucleotide sequence having at least 99% identity to said nucleotide sequence.

(25) The DNA according to any one of (20) to (24) claims 20 to 24, wherein the foreign DNA encodes a peptide, polypeptide, or protein.

(26) A vector comprising the DNA according to any of (20) to (25).

(27) The vector according to (26), which is a plasmid or viral vector.

(28) The vector according to (26) or (27), which is used for gene therapy.

(29) An animal cell transformed with the vector according to any one of (26) to (28).

(30) The animal cell according to (29), which is a vertebrate cell.

(31) A method for producing a peptide, polypeptide or protein, comprising expressing a foreign DNA with the use of the transformed animal cell according to any one of (1) to (6), the animal cell according to (29) or (30), or the transgenic nonhuman mammalian animal according to any one of (7) to (10), and recovering an expression product.

(32) A method for stably expressing a transgene, comprising stably expressing a foreign DNA for a long period of time in the transformed animal cell according to any one of (1) to (6), the animal cell according to (29) or (30), or the transgenic nonhuman mammalian animal according to any one of (7) to (10).

This description includes all or part of the contents as disclosed in the description and/or drawings of Japanese Patent Application No. 2006-314307, which is a priority document of the present application.

BRIEF DESCRIPTION OF THE DRAWINGS

The application contains at least one drawing executed in color. Copies of this patent or patent application publication with color drawing(s) will be provided by the Office upon request and payment of the necessary fee.

FIG. 4 shows spatial dependency of insulation activity. A. Description for design of two targeted transgenic mice XNs and XB as in FIG. 2A. B. Expression pattern of XNs (left panel and upper middle panel) and XB (lower middle panel and right panel). XNs exhibited lacZ expression in the limb (rectangle in left and right panel) and genital bud (middle panels), whereas XB did not. C. Within CNS, XB fragment prevents interaction of enhancer and Hoxd13 promoter, while BB fragment cancels the insulator activity of XB fragment within limbs and genital bud.

FIG. 5 shows the premature expression of Evx2 and Hoxd13 observed in XB targeted transgenic mice. A. Expression of Evx2 and Hoxd13 in 7 dpc embryos of XB transgenic mice is specifically upregulated. Amount of sample RNA was normalized by β-actin. B. Hypothetical scheme for premature expression of these genes in XB transgenic animals. The downstream region of Evx2 recruits repression over Hox complex before 7dpc embryo as preparative stage for Hox expression in wild type or BB targeted transgenic mice. The repression is disrupted by the blocking function by XB fragment and failed to enter into HoxD complex.

FIG. 6 shows a position effect blocker activity of XB fragment. A. Constructs introduced into NIH3T3 cell line. Upper construct I expresses a fluorescent protein, Venus, driven by CAGGS promoter and harbors a neomycin resistant gene enabling G418 selection to obtain stable transformant colonies via transfection in NIH3T3 cells. Lower construct II has a similar constitution with XB blocker fragment on the both sides of the Venus expression marker gene. B. Experimental scheme for the transfection. Stable transformants for both constructs were selected against G418, and maintain the obtained colony for one year of culture. Samples were obtained from each colony after 1, 6 and 12 months and analyzed by FACS. C. 12 colonies for each construct were tested for fluorescence. Construct I without XB fragment apparently decreases the fluorescent positive cells, while XB construct II maintains the fluorescence.

BEST MODES FOR CARRYING OUT THE INVENTION

Figure 1:
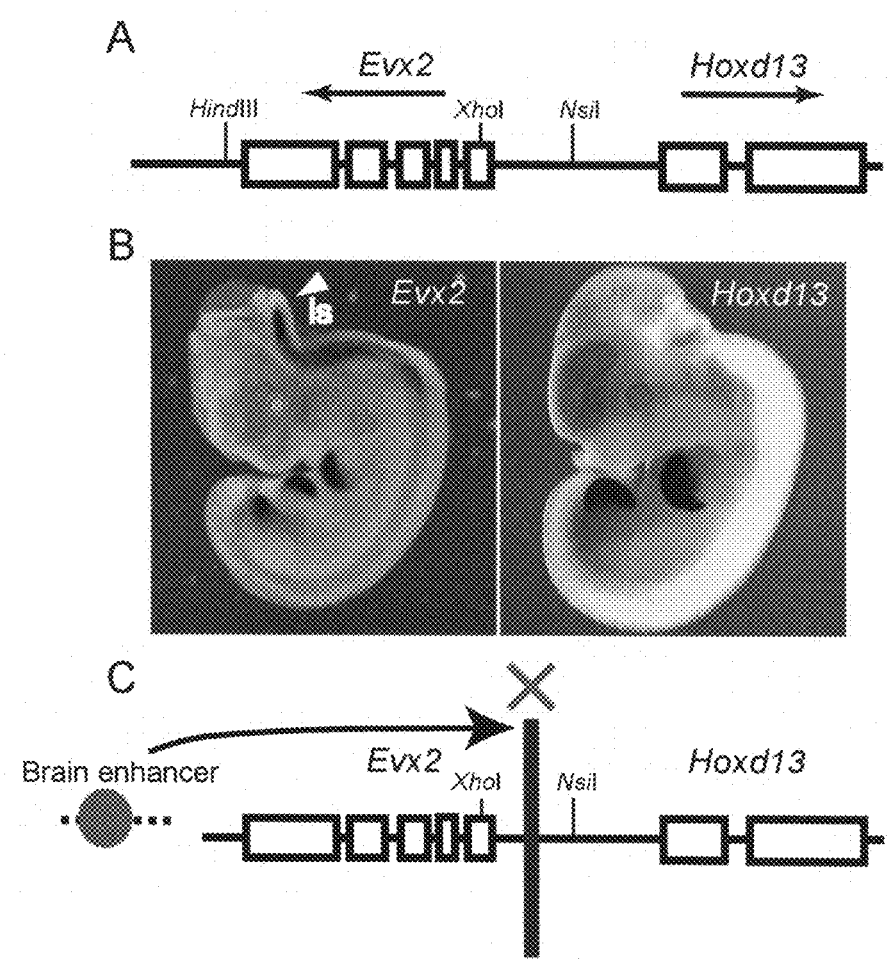
FIG. 1 shows the genomic structures of Evx2-Hoxd13 region and their expression. A. Evx2 and Hoxd13 genes are neighboring in 8 kb distance, encoded on the opposite strand each other. B. Expression pattern of Evx2 (left panel) and Hoxd13 (right panel) at 11 dpc of embryos. Evx2 exhibited its expression in the central nervous system (CNS) as well as in the common expression region with Hoxd13, such as limbs and genital bud. C. Scheme of hypothesis which segregates expression patterns of these genes. Enhancers located 3' of Evx2 can differential accessibility towards Evx2 promoter and Hoxd13 promoter. The intergenic region of the Evx2-Hoxd13 prevents access of enhancer specifically in the CNS but not in limbs.

In the first aspect, the present invention provides an approximately 2.5 kb XhoI-BamHI fragment (or XB fragment) derived from the Evx2-Hoxd13 intergenic region of the animal genome, or a homolog thereof.

The term "XB fragment" as used herein refers to, for example, an approximately 2.5 kb murine XhoI-BamHI fragment as shown in FIG. 3B; i.e., the "XB fragment." In the present invention, however, this term refers to not only the mouse XB fragment but also refers to homologs thereof derived from other animals having a biological function equivalent to that of the XB fragment.

In the second aspect, the present invention provides a DNA containing a foreign DNA, wherein the DNA has been inserted between the two essentially identical XhoI-BamHI fragments (or XB fragments), each approximately 2.5 kb in size, from the Evx2-Hoxd13 intergenic region of an animal genome, or between two essentially identical homologues of the XB fragments having a biological function equivalent to that thereof.

In the third aspect, the present invention provides a DNA containing a foreign DNA, wherein the DNA has been flanked by the two essentially identical XhoI-BamHI fragments (or XB fragments), each approximately 2.5 kb in size, from the Evx2-Hoxd13 intergenic region of an animal genome, or by two essentially identical homologues of the XB fragments having a biological function equivalent to that thereof.

A biological function of the XB fragment or homolog thereof as used in the present invention includes a protecting activity against inhibition caused by the chromosome environment at the site of introduction when a heterologous transgene is introduced into the genome of an animal cell or individual. The term "inhibition" as used herein refers to loss of expression of the inserted foreign gene. Also, the term "homolog" as used herein refers to a DNA fragment on genome corresponding to the XB fragment derived from a different animal species. The homolog essentially comprises a nucleotide sequence that is present in a region between Evx2 gene and Hoxd13 gene on the genome of the animal.

In addition to the above-described protecting activity, the XB fragment or homolog thereof as used herein has an enhancer-blocking activity. The XB fragment or homolog thereof is one of boundary elements located between the Evx2 gene and the Hoxd 13 gene, and because of such boundary element, the enhancer activity cannot reach the promoter beyond the boundary sequence. Such activity is referred to as enhancer-blocking activity or enhancer-insulation activity.

In the present invention, the term "animal" refers to invertebrates, including insects such as drosophilas, silk worms, and armyworms, and vertebrates, such as mammals, avian, amphibians, reptiles, and fish. Vertebrates are preferable, and mammalian animals are more preferable. Examples of mammalian animals include: primates, such as humans, monkeys, and chimpanzees; rodents, such as mice, rats, hamsters, and guinea pigs; and ungulates, such as cattle, goats, sheep, and pigs. Also, animal cells include all cells and cell lines derived from the aforementioned animals. Examples of preferable animal cells include avian cells, such as primary culture cells, mammalian cells, such as primary culture cells, NIH3T3 cells, and HeLa cells. When cells from insects such as armyworms, or the cells, larvae, or chrysalises of silk worms, are used as animal cells, for example, a baculovirus vector can be employed. More particularly, when cells from insects such as armyworms are used, for example, the viral vector AcNPV can be employed. When the cells, larvae, or chrysalises of silk worms are used, for example, the viral vector BmNPV can be employed.

The sequences of the XB fragment and homologs thereof as used herein can be obtained using the databases of the GenBank (NCBI, U.S.A.) and EMBL (EBI, Europe) for example. As the searching system, for example, BLAST (NCBI) can be used (Toshihisa Takagi and Minoru Kanehisa (ed.), Genome net no database no riyou hou ("Utilization of genome net database"), vol. 2, 1998, Kyoritsu Shuppan., Tokyo, Japan).

Examples of nucleotide sequences of the XB fragment and homologs thereof are mouse-, human- and chicken-derived nucleotide sequences as shown in SEQ ID NOS: 1, 2, and 3, respectively, and nucleotide sequences having at least 99%, preferably at least 99.5%, and more preferably at least 99.9% identity to the mouse-, human- and chicken-derived nucleotide sequences. As used herein, the term "% identity" means a percentage (%) of the number of identical nucleotides relative to the total number of nucleotides, when any of the aforementioned sequences is aligned with the other sequence with or without introduction of gaps. As homologue searching algorisms or % identity determining algorisms, BLAST or FASTA can be used for example.

The XB fragment and homologs thereof can be prepared by polymerase chain reaction (PCR) using primers prepared based on the above nucleotide sequences and using genomic DNAs prepared from the animal cells or tissues as templates, and by gene recombination techniques.

The primers have 15-50 nucleotides, preferably 17-30 nucleotides, and more preferably 20-25 nucleotides, normally.

PCR comprises three reaction steps of denaturation, annealing, and extension. For example, PCR comprises a step of denaturing double-stranded DNA at 94° C. for 15 to 60 seconds, a step of annealing a primer to a single-stranded template DNA at 55° C. for 30 to 60 seconds, and a step of extending a primer at 72° C. for 30 seconds to 10 minutes. A cycle of the three reaction steps of denaturation, annealing, and extension is repeated 20 to 40 times, for example. Further, heating at 94° C. for 30 seconds to 5 minutes may be carried out prior to the initiation of the cycles, and extension may be carried out at 72° C. for 30 seconds to 10 minutes after the completion of the cycles. PCR involves the use of a thermostable polymerase, such as Taq polymerase (e.g., Ampli Taq or TaKaRa Taq). Also, PCR requires about 20-200 µM dNTPs (N=A, T, C and G) and about 1.5-2.5 mM $Mg^{2+}$ for example, in the reaction medium. PCR can be conveniently carried out with the use of a commercially available automated apparatus (e.g., RoboCycler (Funakoshi, Japan) or GeneAmp (Perkin Elmer)). Since the size of the amplified products is a kilo base order, the amplified product can be detected by, for example, agarose gel electrophoresis. Regarding the PCR method, a reference may be made to, for example, Sekiya and Fujinaga (ed.), PCR Hou Saizensen (PCR Method Frontier), Proteins, Nucleic Acids, Enzymes, Kiso kara Ouyou made ("From basic to applications"), vol. 41, No. 5, extra edition of April 1996, Kyoritsu Shuppan, Tokyo, Japan.

Template DNA can be prepared from tissues or cells by conventional techniques, such as proteinase/phenol extraction method or proteinase/phenol/chloroform method.

In the present invention, the foreign DNA can encode a peptide, polypeptide, or protein. For example, the foreign DNA can encode a peptide, polypeptide, or protein that is useful in the food or pharmaceutical industries, such as a hormone, an enzyme, a nerve transmitter substance, or an antibody. Also, the foreign DNA may encode a proform or preproform of the aforementioned peptide, polypeptide, or protein, or a signal peptide conjugate. The foreign DNA can be synthesized by obtaining a nucleotide sequence thereof from the GenBank or EMBL database or published papers for example, and using a DNA automatic synthesizer and gene recombination techniques.

DNA can be synthesized by gene recombination techniques as described in, for example, Sambrook et al., Molecular Cloning: A Laboratory Manual, Cold Spring Harbor Laboratory Press, 1989. Briefly, the target DNA is inserted into a vector for prokaryotes, such as *E. coli* or *Bacillus subtilis* (e.g., a commercially available plasmid vector), which is then transformed into prokaryotic cells, followed by proliferation of the cells. Following recovery of the vector, the target DNA can be cleaved out with the use of adequate restriction enzymes.

In the present invention, the XB fragment or homologues thereof, or the two essentially identical XB fragments or homologues thereof, and the foreign DNA are prepared in accordance with the procedure as described above, and the foreign DNA is then ligated so as to flank the XB fragment or homolog thereof. Alternatively, the foreign DNA is ligated to a site between the two essentially identical XB fragments or homologues thereof. The ligation can be conducted using a DNA ligase via formation of a sticky or blunt end by action of an adequate restriction enzyme.

The term "two essentially identical" as used herein means that the nucleotide sequences of two XB fragments or homologues thereof have at least 99%, preferably at least 99.5%, and more preferably at least 99.9% sequence identity to each other. Preferably, the nucleotide sequences of two XB fragments or homologues thereof are identical to each other.

The term "flank(ing)" as used herein means that DNAs are ligated to each other in a substantially adjacent manner. An intervening sequence(s) may be present in between the DNAs. The intervening sequence can include, for example, a partial sequence of a restriction enzyme site, a linker sequence, or a control sequence (e.g., a promoter, an enhancer, or a ribosome-binding site).

The DNA of the present invention may further comprise a control sequence, such as a promoter, enhancer, or terminator, where necessary. Examples of the promoter include tissue-specific promoters, viral promoters, and the like, such as CAGGS promoter and β-actin promoter. The promoter is generally linked to the 5' end of a foreign DNA sequence.

The present invention further provides a vector comprising the aforementioned DNA containing a foreign DNA.

The vector of the present invention may be of any type, provided that the vector comprises the above-defined DNA and is capable of causing a recombination or insertion at random or a homologous recombination on the genome of an animal cell. A preferable vector is a plasmid or viral vector. Examples of plasmid vectors include pGT-N28 (New England Bio Labs), pBluescript II SK⁺ (Stratagene), pSP72, and pPNT vectors, and examples of viral vectors include adenovirus, adeno-associated virus, retrovirus, and lentivirus vectors, although the vectors are not limited thereto. When cells from insects such as armyworms, or cells, larvae, or chrysalises of silk worms, are used as animal cells, for example, a baculovirus vector can be employed. In the case of the cells from insects such as armyworms, more particularly, the AcNPV viral vector can be employed, and the BmNPV viral vector can be employed when the cells, larvae, or chrysalises of silk worms are used.

It is convenient for a vector to contain a cloning site, such as a multicloning site, in order to ligate the DNA of the present invention to the vector. Since the multicloning site contains a plurality of unique restriction sites, the DNA of the present invention can be easily inserted at an appropriate position of the restriction sites.

The vector of the present invention may further comprise a selection marker. Examples of selection markers include positive selection markers for transformed cells, such as drug-resistance gene markers (e.g., a neomycin resistant gene, a hygromycin resistant gene, and a blasticidin resistant gene) and/or negative selection gene markers (e.g., an HSV thymidine kinase (HSV-tk) gene and a diphtheria toxin A gene). Negative selection is useful for selectively eliminating a non-homologous recombinant cell in the presence of a drug, such as an anti-herpes drug, FIAU, or ganciclovir, thereby allowing selection of a homologous recombinant cell.

The vector of the present invention may further comprise loxP sequences at each end of the DNA of the present invention, in order to enhance the efficiency of homologous recombination on the genome of an animal cell. The so-called Cre-loxP sequence (R. Kuhn et al., Science, 1995, 269: 1427-1429) can be used (see, for example, Aizawa Shinichi, "Gene targeting—Generation of mutant mouse using ES cell," Biomanual Series 8, Yodosha, Tokyo, Japan, 1995).

The vector of the present invention prepared by the above-described way may be used to transform or transfect an animal cell with the vector. Examples of methods for introducing a vector include, but are not limited to, a microcell method, electroporation, a liposome method, a calcium phosphate method, and a DEAE-dextran method.

Examples of animal cells include cells as exemplified above. Preferably, the animal cells are differentiated. Preferable animal cells are vertebrate cells, and mammalian cells or avian cells are particularly preferable. Examples of mammalian cells include primary culture cells, NIH3T3 cells, and HeLa cells, and examples of avian cells include primary culture cells.

The transformed animal cell of the present invention can be produced in the following manner, for example. Specifically, this method comprises: a step of preparing two essentially identical XhoI-BamHI fragments (or XB fragments), each approximately 2.5 kb in size, from the Evx2-Hoxd13 intergenic region of an animal genome, or two essentially identical homologues of the XB fragments having a biological function equivalent to that thereof; a step of forming a DNA containing a foreign DNA, wherein the DNA has been inserted between the XB fragments or homologues thereof or flanked by the XB fragments or homologues thereof; a step of inserting the obtained DNA into a vector; and a step of introducing the vector into an animal cell to integrate the DNA into the genome of the cell, thereby resulting in a transformed animal cell.

According to the above method, the DNA is incorporated into the cell genome at random or by homologous recombination with the sequence of the native XB fragment or homolog thereof on the genome. The integration may be carried out between those from the same or different species in relation of the cell genome and the DNA.

In general, the recombination is a reaction for exchanging or moving a foreign DNA between the same or different chromosomes. Homologous recombination takes place between DNA fragments having very similar sequences, while non-homologous recombination (or random insertion) takes place between sequences that are not similar or are less similar to each other. In mammalian cells, a foreign DNA is less likely to be integrated into a specific site of the genome by homologous recombination, but random insertion is known to occur at high frequency. According to the present invention, DNA may be integrated into the genome by either homologous recombination or random insertion, as described above. Endogenous genes remain unchanged in the case of random insertion.

The present invention further provides a transgenic nonhuman mammalian animal obtained by the following steps of: preparing a foreign DNA-containing DNA, which has been inserted between two essentially identical XhoI-BamHI fragments (or XB fragments), each approximately 2.5 kb in size, from the Evx2-Hoxd13 intergenic region of the animal cell genome or two essentially identical homologues of the XB fragments having a biological function equivalent to that thereof, or which has been flanked by the XB fragments or homologues thereof, followed by inserting the DNA into a vector; introducing the obtained vector into an egg cell or embryonic stem (ES) cell derived from the nonhuman animal; transplanting the egg cell or ES cell to a surrogate female parent animal; and obtaining a chimeric animal comprising the foreign DNA via childbirth.

The DNA containing a foreign DNA is as defined above.

The transgenic nonhuman mammalian animal of the present invention can be prepared in the following manner, for example. Specifically, this method comprises steps of: preparing a DNA containing a foreign DNA, wherein the DNA has been inserted between two essentially identical XhoI-BamHI fragments (or XB fragments), each being approximately 2.5 kb in size, from the Evx2-Hoxd13 intergenic region of the genome of the animal, or between homologues of the XB fragments having a biological function equivalent to that thereof, or alternatively constructing a DNA containing a foreign DNA flanked by the XB fragments or homologues thereof, and then inserting the obtained DNA into a vector; introducing the obtained vector into an egg cell or embryonic stem (ES) cell of a nonhuman animal; transplanting the egg cell or ES cell to a surrogate female parent animal; and obtaining a chimeric animal comprising the foreign DNA via childbirth.

Examples of nonhuman mammalian animals include rodents, such as mice, rats, guinea pigs, and hamsters, and ungulates, such as cattle, sheep, goats, and pigs. A preferable nonhuman mammalian animal is a mouse.

Preparation of the Chimeric Animal and Offspring Animals Thereof According to the present invention is further described in detail.

The chimeric animal of the present invention can be prepared by a method comprising directly injecting a targeting vector into a fertilized egg and transplanting the resulting egg into the surrogate parent, a method involving the use of embryonic stem (ES) cells, and other methods.

A method involving the use of a fertilized egg (an egg cell) is described below.

The DNA or vector of the present invention is microinjected via a microinjection method into the male pronucleus of a fertilized egg collected from a crossed nonhuman female animal, and the fertilized egg is transplanted into the oviduct of the female animal (i.e., the surrogate parent), which had previously been crossed with a sterilized male animal, in order for the animal to give birth to chimeric animals.

Part of the tissue of the chimeric animal is removed to extract DNA therefrom, and an animal, which comprises a transgene containing a foreign DNA of interest integrated into the chromosome, can be selected by conventional techniques, for example, hybridization techniques such as Southern hybridization or in situ hybridization, or genomic PCR. In this case, hybridization can be carried out using a probe which is labeled with a fluorescent or radioactive label and comprises the sequence complementary to the foreign DNA. Examples of fluorescent labels include fluorescamine and derivatives thereof (e.g., FITC), rhodamine and derivatives thereof (e.g., tetramethylrhodamine isothiocyanate, Texas Red, and Rhodamine Red-X), and cyanine fluorescent dyes (e.g., Cy3 and Cy5).

By crossing between the chimeric animals created in the above-described manner or between the chimeric animal and a wild-type animal, heterozygotes are obtained, which are subsequently crossed to prepare and select homozygotes.

The method involving the use of ES cells is next described.

The ES cell is a cell line established by culturing undifferentiated cells in the inner cell mass of a blastocyst or 8-cell stage embryo after fertilization and repeating dissociation and passage of the cell mass, which cell line can continue proliferation while maintaining an undifferentiated state. Examples of known mouse ES cell lines include D3 cell line, E14TG2a cell line, TT2 cell line, AB-1 cell line, J1 cell line, and R1 cell line.

The thus-prepared targeting vector is introduced into ES cells via conventional techniques, such as the microcell method, electroporation, the liposome method, the calcium phosphate method, and the DEAE-dextran method.

Whether or not the recombination of interest (including homologous recombination or non-homologous recombination) has occurred in the obtained ES cells can be confirmed by Southern hybridization, Southern blotting, in situ hybridization, and genomic PCR, using probes or primers, or by other means. Thus, ES cells in which the recombination has occurred are selected. Thereafter, the selected ES cells are introduced into the blastocyst or 8-cell stage embryo of a wild-type animal, transplanting the ES cell-containing embryo into the uterus of a pseudopregnant surrogate parent animal, and having the surrogate parent animal to give birth to offspring, thereby preparing a chimeric animal.

As methods for introducing ES cells into embryos such as blastocysts, microinjection and aggregation methods are known, and either method can be employed. In case of mouse, a female mouse that has been subjected to superovulation with a hormone is crossed with a male mouse to obtain an early embryo. When the blastocyst is used as an embryo into which a recombinant ES cell has been introduced, the early embryo is recovered from the uterus 3.5 days after fertilization. When the 8-cell stage embryo is used, the early embryo is recovered from the uterus 2.5 days after fertilization. The recombined ES cells are injected in vitro into the thus-recovered embryo using a targeting vector to generate a chimeric embryo.

A pseudopregnant female animal used as a surrogate parent can be obtained by crossing a female animal in the normal estrous cycle with a male animal sterilized by vasoligation or the like. The chimeric embryo as generated above is transplanted into the uterus of a pseudopregnant animal to become pregnant and give birth to offspring. Thus, chimeric animals can be obtained. To ensure the embryo implantation and pregnancy of a chimeric embryo, it is preferable that a female animal from which fertilized eggs are collected and a pseudopregnant animal used as a surrogate parent be prepared from female animals in the same estrous cycle.

When animal individuals derived from an ES cell-transplanted embryo are obtained from such chimeric mice, introduction of ES cells into the chimeric mouse germ line can be confirmed based on the development of hair color from ES cells in offspring individuals in the case of, for example, mice resulting from the crossing of a chimeric animal with a pure line animal. Introduction of ES cells into the germ line can be confirmed using a variety of traits as indicators. From the viewpoint of easy confirmation, use of hair color as an indicator is desirable. Alternatively, DNA may be extracted from a part of the body (for example, the caudal portion) and subjected to Southern blot analysis or PCR assays to select the germ line of interest.

Animals comprising the germ lines into which recombinant ES cells have been transplanted into embryos have been introduced are thus selected, the chimeric animals are allowed to proliferate, and animal individuals into which the transgene comprising a foreign DNA of interest have been introduced can be obtained. The resulting heterozygote (+/−) animals are crossed or a chimeric animal is crossed with a wild-type animal. Thus, a target homozygote [(−/−)](+/+) animal can be obtained. The thus-obtained animal is genetically inherited to an offspring animal. Thus, the nonhuman mammalian animal of the present invention includes both a chimeric animal comprising foreign DNA and offspring thereof.

Regarding the above gene targeting method, reference can be made to Aizawa Shinichi, "Gene Targeting-Generation of Mutant Mouse Using ES cell," Bio-manual Series 8, Yodosha, Tokyo, Japan, 1995.

The present invention further provides a method for producing a peptide, polypeptide, or protein comprising expressing a foreign DNA using any of the above transformed animal cells and recovering the expressed product.

Foreign DNA can be expressed using the above transgenic nonhuman mammalian animal. Specifically, the tissue or body fluid in which foreign DNA has been expressed is removed from the animal, and the expressed product can be purified by employing conventional purification techniques (see below) in combination. In order to conduct site-specific expression, for example, an organ, an organ-specific transit peptide, or DNA encoding a signal or milk secreting signal can be ligated to a foreign DNA.

The animal cells of the present invention can be cultured in a medium suitable for animal cell culture (e.g., Dulbecco's MEM, alpha-MEM, and DMEM/F12 media) at an adequate temperature (e.g., 25 to 40° C.) to express a foreign DNA. When the foreign DNA has a signal sequence, the expressed product is secreted outside the cell. Thus, the expressed product can be recovered from the medium.

A peptide, polypeptide, or protein as the expressed product can be purified by adequately combining conventional techniques: such as gel filtration; chromatography techniques, such as ion-exchange chromatography, affinity chromatography, hydrophobic interaction chromatography, and HPLC; salting-out; centrifugation; and ultrafiltration.

The expressed product can be identified and quantified by, for example, immunological analyses using specific antibodies (e.g., enzyme-linked immunoassay, fluorescence immunoassay, sandwich assay, or Ouchterlony method), methods for assaying a molecular weight, such as HPLC or SDS-PAGE, and the like.

The present invention further provides a method for stably expressing a transgene, comprising stably expressing a foreign DNA for a long period of time in the above-described transformed animal cell or nonhuman mammalian animal.

As used herein, the term "transgene" refers to a foreign DNA as defined above, and the transgene preferably encodes a peptide, polypeptide, or protein, for example.

As verified in the working examples below, a transformed animal cell comprising the DNA of the present invention introduced into its genome via recombination (including either homologous or non-homologous recombination) can produce a peptide, polypeptide, or protein encoded by a foreign DNA for a long period of time, i.e., for a year or longer. Based on such facts, a transgene would be stably expressed in the nonhuman mammalian animal.

When a transgene encodes a peptide, polypeptide, or protein that is therapeutically effective, in particular, the vector of the present invention can be used for gene therapy for a human patient. In such a case, the vector may be injected directly into a lesion. Alternatively, the vector may be incorporated into liposomes, and in particular, positively-charged liposomes (e.g., the positively-charged cholesterol derivative described in Mamoru Nakanishi et al., Proteins, Nucleic Acids, Enzymes, Vol. 44, No. 11, 1590-1596, 1999, Kyoritsu Shuppan Co., Ltd., Tokyo, Japan; this derivative can transfer a foreign gene into a nucleus, as well as into a cell) or high molecular nanoparticles (e.g., Younsoo, Bae and Kazunori Kataoka, Seikagaku (Journal of Biochemistry), Vol. 78, No. 9, 882-887, the Japanese Biochemical Society, Tokyo, Japan, 2006), and the resultant can be administered parenterally via intravenous injection, for example. Diseases are not particularly limited, and examples of the diseases include Huntington's disease and cancers.

Furthermore, when a foreign gene with unknown functions is introduced into the transgenic animal of the present invention, the transgenic animal is capable of stably expressing the gene for a long period of time. Accordingly, the results of observation of influences of such gene on an organism can be utilized for elucidation of biological functions.

The present invention will be hereafter described in more detail with reference to the following examples, although the technical scope of the present invention is not limited thereto.

EXAMPLES

(1) Experimental Procedures

Targeted Transgene

Hoxd9/lacZ indicator transgene is inserted into HindIII site just downstream of the Evx2 gene by electroporation into R1 ES cells together with test fragment at the 5' flanking the transgene. ES cells were selected with neomycin resistance and homologous recombinants were isolated by genomic Southern hybridization as in the previous report (T. Kondo and D. Duboule, Cell, 1999, 97: 407-417). Chimeras were created with these homologous recombinant ES cells to establish targeted transgenic animals.

Cell Culture

NIH3T3 cells were cultures with Dulbecco's MEM supplemented with 10% FBS. Constructs were introduced by electroporation. 12 colonies from each pool of transformants with two constructs were randomly isolated and used for further test. The present inventors continued culturing these transformants and observed fluorescence of them at 1, 6 and 12 months after starting of the culture.

Gene Expression

Staining of β-galactosidase and in situ hybridization has been done with established protocol. Hoxd13 probe is described previously. Evx2 probe has been derived from XbaI-BamHI genomic fragment of Evx2 gene corresponding to 3' UTR of Evx2 gene.

The present inventors have also observed the expression of Evx2 and Hoxd13 genes with real-time PCR using Corbett with Invitrogen Platinum SYBRGreen PCR kit. The present inventors isolated mRNA of 7 dpc embryos from three plagues of wild type matings, 6 plagues from XB taregeted transgenic heterozygotic mice matings, and made a pool of cDNA from each litter of embryos. In order to control the amount of cDNA, the present inventors have carried out PCR with β-actin and determined dilution ratios of cDNA.

Primers used are as follows.

```
β-actin:
5'-CATGTTTGAGACCTTCAACAC-3'      (SEQ ID NO: 4)

5'-GTGATGACCTGGCCGTCAGG-3'       (SEQ ID NO: 5)

Evx2:
5'-GGTGTCCAGTTGTGGCTGATC-3'      (SEQ ID NO: 6)

5'-CTACCACGCATTCCCTGTCTG-3'      (SEQ ID NO: 7)

Hoxd13:
5'-GGTTTCCCGGTGGAGAAGTAC-3'      (SEQ ID NO: 8)

5'-TGGACACCATGTCGATGTAGC-3'      (SEQ ID NO: 9)
```

The present inventors ran PCR triplicate for each pool of cDNA and calculated the amounts of products with standard curve made by sequential dilutions of isolated cDNAs for β-actin, Evx2 and Hoxd13.

(2) Results

Difference in Expression Profiles of Evx2 and Hoxd13

Evx2 gene locates next to Hoxd13 within 8 kb distance, and is encoded on the other strand of DNA than other HoxD genes (FIG. 1A). Evx2 shows distinct expression profile to its neighboring gene Hoxd13 after 10 days post coitum (dpc) of embryos (FIG. 1B), although the expression profiles earlier are almost identical each other. Evx2 starts to express in central nervous system (CNS) at 10 dpc embryos, especially prominent in isthmus, whereas Hoxd13 showed no such anterior expression pattern in any of embryonic and fetal period (FIG. 1B). In previous study, we have created mice harboring series of insertion of Hoxd9/lacZ marker transgene surrounding of Evx2 by using homologous recombination system in ES cells (FIG. 2A) (T. Kondo and D. Duboule, Cell 1999, 97: 407-417). Transgene inserted in immediately downstream of Evx2 poly(A)+ signal (relI) mirrors Evx2 expression, while another transgene at the middle of Evx2 and Hoxd13 initiation codons (relO) resembles Hoxd13, which lacks expression in central nervous system at 11 dpc embryos (FIG. 2B) (T. Kondo and D. Duboule, Cell 1999, 97: 407-417). Enhancer activities driving CNS, digital and genital expression of these genes are located at the region about 250 kb downstream from Evx2 (Spitz et al., 2003). These results suggested that an enhancer blocker element (insulator) exists around promoter region of Evx2, which prevents enhancer interaction to Hoxd13 in CNS (FIG. 1C) (T. Kondo and D. Duboule, Cell 1999, 97: 407-417; M. Kmita et al., Development, 2002, 129: 5521-5528).

Figure 2:
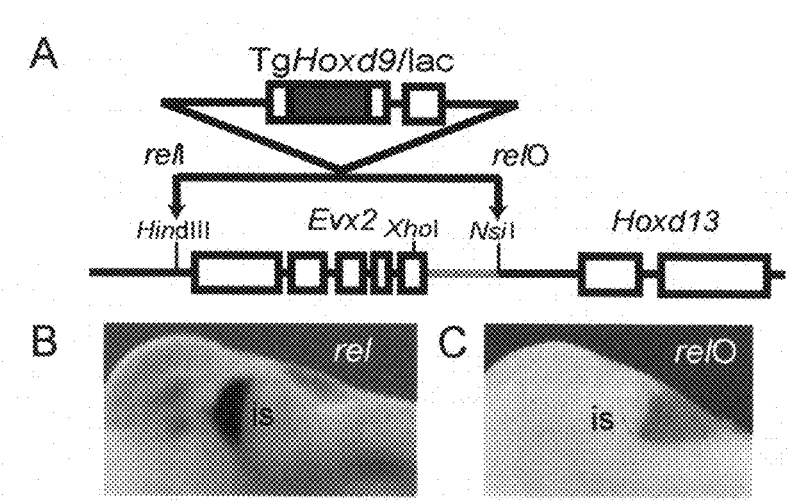
FIG. 2 shows Hoxd9/lacZ marker transgene expression patterns of targeted transgenic mice. In relO transgenic mice line, Hoxd9/lacZ transgene is inserted into the middle of Evx2 and Hoxd13 genes. In relI line, Hoxd9/lacZ transgene is inserted into the region immediate downstream of Evx2 by gene targeting technique using ES cells (A). The resulting ES cells were injected to establish the mice. LacZ staining pattern indicates that relO mice have no brain expression as observed in Hoxd13 in situ hybridization (B), while relI exhibits clear isthmus expression as Evx2 (C).
Figure 3:
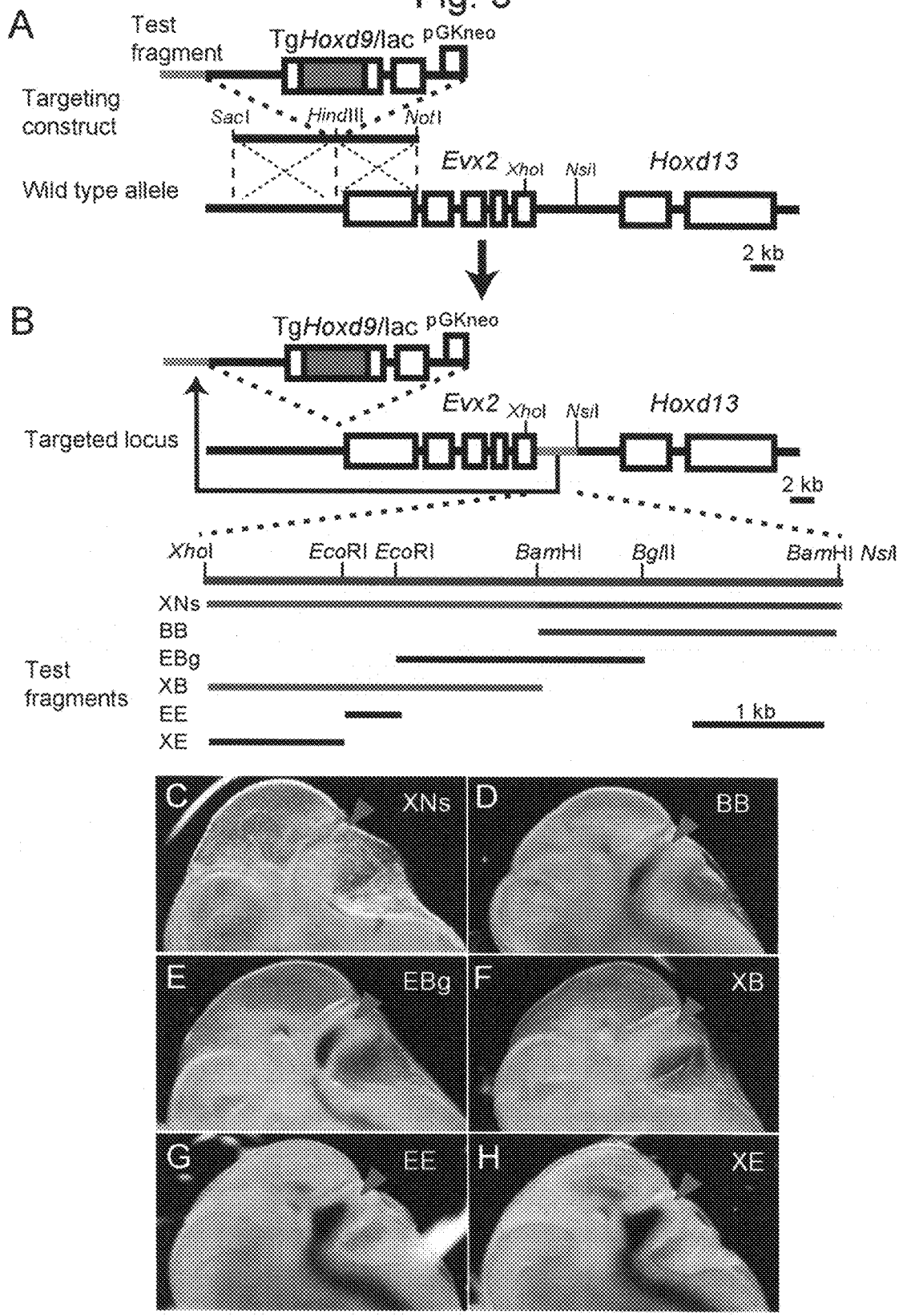
FIG. 3 shows the results of the analysis of the insulator fragment using targeted transgene experiments. A. Scheme of experimental design. Hoxd9/lacZ transgene with an insulator candidate fragment is inserted into the region immediate downstream of Evx2 by gene targeting technique using ES cells. The resulting ES cells were injected to establish the mice. B. XhoI-NsiI (XNs) fragment indicated in red color is dissected into three fragments, i.e., BamHI-BamHI (BB), EcoRI-BglII (EBg) and XhoI-BamHI (XB) fragment, and translocated together with Hoxd9/lacZ reporter transgene. LacZ staining against 11 dpc embryos exhibited XNs (C) and XB (F) blocked the brain expression of lacZ gene, while BB (D) and EBg (E) failed. Based on these results, XB fragment was further divided into XhoI-EcoRI (XE) and EcoRI-EcoRI (EE) and the present inventors made targeted transgenic mice with similar configuration. Both the XE (G) and EE (H) exhibited brain expression and did not exhibit any trace of insulation activity.

Candidate sequences for boundary function were translocated at the region of immediate downstream of Evx2, together with Hoxd9/lacZ as reporter, by homologous recombination using ES cells (FIG. 2A, FIGS. 3A and 3B). The resulted ES cells with translocated DNA were injected into blastocysts to create mouse embryos. Either of these chimeras or progenies from chimeras were stained for β-galactosidase activity. If the introduced fragment has activity as insulator, lacZ staining pattern is expected to resemble Hoxd13-like pattern, otherwise lacZ pattern should exhibit as Evx2 with CNS expression. From the previous observations (T. Kondo and D. Duboule, Cell 1999, 97: 407-417), the boundary sequence is assumed to locate between Evx2 promoter and the NsiI site at the middle of Evx2 and Hoxd13 site, namely the relO transgene insertion site (T. Kondo and D. Duboule, Cell 1999, 97: 407-417) (FIG. 2). Staining pattern of lacZ showed Hoxd13 like expression when whole sequence from the candidate region, namely the 5 kb fragment between XhoI site in the first exon of Evx2 gene and NsiI site for relO transgene insertion, was inserted together with lacZ reporter transgene, thus the XhoI-NsiI fragment blocked brain enhancer activity (FIG. 3C). This observation evaluates the experimental design. The present inventors have divided the XhoI-NsiI (XNs) fragment into 3 overlapping pieces of about 2 kb each, i.e., XhoI-BamHI (XB), EcoRI-BglII (EBg) and BamHI-BamHI (BB) fragments, from the side of Evx2 initiation codon (FIG. 2B). Both of the transgenic mice harboring EBg fragment and BB fragment, respectively, showed Evx2 like lacZ expression pattern (FIGS. 3D and 3E), indicating that they failed to block interaction of the CNS enhancer towards Hoxd9/lacZ promoter (FIG. 3). On the other hand, the XB fragment showed boundary activity as brain expression of transgene completely vanished (FIG. 3F). The present inventors have made further dissection of the XB 2.5 kb fragment into three pieces (FIG. 3B). None of these shorter fragments showed boundary activity and blocked enhancer interaction (FIGS. 3G and 3H). This indicated that a certain length of DNA containing multiple protein binding sites, which are dispersed within this 2.5 kb fragment, is required for proper boundary function and that the boundary activity is a consequence of complex DNA-protein interaction (FIG. 3).

Two functional Sequences Contain Evx2-Hoxd13 Insulator Sequence

Comparison of lacZ expression patterns of the XNs targeted transgenic and the XB transgenic mice showed distinctive differences (FIGS. 4A and 4B). As shown in FIG. 3, both the fragments blocked the brain-CNS expression of inserted lacZ reporter gene. On the other hand, while we could observe the staining of lacZ from the XNs mice in the limbs and external genitalia as Hoxd13 expression, the XB mice did not show any trace of staining in limbs and genital bud (FIG. 4B). These results suggested that the XB fragment is a constitutive insulator, and in addition, the specificity of the blocker activity is determined by the sequence in the BamHI-NsiI site (BNs), outside of the core blocker sequence, XhoI-BamHI. The sequence in this BNs fragment may counteract or cancel the blocker activity of the XB fragment in the limbs and genitalia, and posterior Hoxd genes can have expression in the limbs and genitalia (FIG. 3C). Thus, the blocker sequence in Evx2-Hoxd13 system can be divided into two units, constitutive blocker and blocker regulator.

Lethality of the Targeted Transgenic Mice and Hoxd13 Expression

To further investigate the enhancer blocking activity of XB fragment, the present inventors tried to observe expression patterns of Hoxd13 and Evx2 patterns in the targeted transgenic mice with XB fragment. After collection of several litters of 11.5 dpc embryos, the present inventors found no homozygotic targeted transgenic mice of XB fragment. Further analysis exhibited that homozygous allele could not be found even among 7.5 dpc embryos (Table 1), while one of the control lines with BB targeted transgene yielded homozygotic transgenic mice at 8.5 and 11.5 dpc embryos (Table 1).

TABLE 1

Segregation of genotype in internal breeding of targeted transgenic mice

| Stage (dpc) | Wild type (−/−) | XB/− | XB/XB |
|---|---|---|---|
| 7.5 (n = 40) | 8 (20%) | 32 (80%) | 0 |
| 8.5 (n = 32) | 13 (40.6%) | 19 (50.9%) | 0 |
| 11.5 (n = 46) | 12 (26.1%) | 34 (73.9%) | 0 |

| Stage (dpc) | Wild type (−/−) | BB/− | BB/BB |
|---|---|---|---|
| 8.5 (n = 32) | 7 (21.9%) | 12 (37.5%) | 13 (40.6%) |
| 11.5 (n = 37) | 8 (21.6%) | 26 (70.3%) | 3 (8.11%) |

As the lethality could not be segregated after more than 5 generations of out-breeding, the phenotype is closely linked to the presence of additional copy of XB fragment next to the Evx2 gene. To investigate the possible misregulation of Hoxd13 or Evx2 transcription by this insertion of transgene, the present inventors tested the expression of Hoxd13 and Evx2 in the 7 dpc embryos from XB transgenic line (FIG. 5A). Series of pools of cDNA prepared from one litter of embryos were subjected for real-time PCR to analyze gene expression. Three cDNA pools of embryos from wild type mice internal breeding and six litters from XB mice internal breeding were constructed. While wild type has almost no expression of Hoxd13 and Evx2, cDNA pools from XB breeding apparently showed expression of these genes, although the magnitude of expression varied among the litters (FIG. 5A). These results suggested that XB transgenic line has immature expression of Hoxd13 or Evx2 earlier than 7 dpc embryos and the lethality observed in these mice corresponds to this immature expression. In previous works, we suggested the region outside of the HoxD complex is responsible for early repression of genes in the HoxD complex and prevent premature expression of Hoxd genes before 7 dpc embryo (T. Kondo and D. Duboule, Cell 1999, 97: 407-417). Presence of extra copy of the XB fragment, which forms constitutive boundary with absence of regulatory sequence, in between this repressive region and HoxD complex may interfere the repression recruited by this region and release expression of Hoxd genes, in this case Evx2 and Hoxd13 genes, prematurely (FIG. 5B). Thus, these results suggested that XB fragment have protection activity against repression as well as enhancer blocker activity.

The Protection Activity Against Repression from Chromosomal Environment

When an exogenous gene is introduced within a genome, the transgene often suffered from repression caused by chromosomal environment of the insertion site after passage of time. As a boundary sequence separates the domains of a chromosome, it has to interfere such repressive position effect as well as enhancer interaction (F. Recillas-Targa et al., Proc. Natl. Acad. Sci., U.S.A., 2002, 99: 6883-6888). Since our observation suggested that the XB fragment has protection activity against repression, we have further investigated the possibility to prove whether the XB fragment works for position effect protection also at the random position in the genome.

Two of the constructs to express fluorescent protein, Venus, were prepared for this analysis. Construct I had no boundary fragment and Construct II had the fragment (XB; FIG. 3) on both sides of Venus-marker gene (FIG. 6A). Both of these constructs also harbor a resistant marker against antibiotics, neomycin, to facilitate isolation of stable transformants. These constructs were introduced to NIH3T3 cells and selected for neomycin resistance for 10 days to get randomly integrated transformed cell lines (FIG. 6B). 12 stably transformed colonies from each construct were picked up. Most of the clones contain transgene in low copy number (1-5 copies) estimated by genomic Southern hybridization. After the colony isolation, colonies were kept without neomycin and observed maintenance of fluorescence by FACS (FIG. 6B). After 1 month of culture without neomycin, most of the cell clones maintained expression of fluorescence by Venus except for one from Construct II (flanked by XB-blocker) probably due to the disruption of transgene from the very beginning of the experiments (FIG. 6C). Further 5 months of culture (total 6 months) showed dramatic difference between transfected colonies from Construct I and II (FIG. 6C). 7 out of 12 Construct I clones lost fluorescence almost completely, while only 3 out of 12 Construct II lost fluorescence. On the other hand, 1 clone from Construct I transformants still contained fluorescent cells more than 75% of total cells, when 4 clones from Construct II showed fluorescence in most of the cells (FIG. 6C). After 1 year of culture, 9 of Construct I clones lost fluorescence, whereas 7 clones from Construct II transformants maintained fluorescence nearly completely (more than 75% of cells kept fluorescent by FACS analysis). In overall, XB-flanked Venus marker apparently maintained fluorescence more efficiently than non-flanked marker (FIG. 6C). These results strongly suggested that XB fragment have position effect protection activity.

Tissue Specificity of Enhancer Blocker Function

The expression profiles of Evx2 and Hoxd13 genes have many of common aspects such as initiation timing and expression in the future digit domain. However, they exhibit difference in expression in the brain and spinal cord. Evx2 has strong expression in these central nervous systems (CNS) while Hoxd13 does not. Several evidence indicate that these differences were due to the difference in the ability for association of enhancers toward promoters. Interestingly, both the enhancers to drive these genes in the digit and brain locate in the same orientation from the HoxD complex, i.e., beyond Evx2 from Hoxd13. It suggested that blocking activity (insulator activity) works in the tissue specific mode than constitutive blocking. In this work, we exhibited that the functional region for this insulation can be divided into two units, the 2.5 kb fragment which has constitutive blocker activity, and another functional sequence which regulates the tissue specificity of the insulation activity. The detailed mechanistic basis of interaction between these two functional sequence remains to be cleared. However, the series of targeted transgene clearly indicated that the presence of boundary regulator interfere the boundary sequence to function in digit and genitalia, and thus, chromatin constitution acquires tissue specific dynamics.

In this work, we demonstrated that the Evx2-HoxD boundary works in tissue and time specific mode and this boundary element can be divided into two functional fragments, constitutive boundary element and boundary regulator fragment which gives tissue specificity to constitutive boundary. The constitutive boundary element can protect promoters from repressive influence from chromosomal environments when it is inserted with the promoters. It also suggests that this fragment can provide a good tool for stable expression of exogenous promoter in eukaryotic cells.

Stable Expression of Transgene in Transgenic Mouse

The Venus-expressing construct (Construct I), in which Venus has not been put between the XB fragments, and Construct II having the XB fragments at each end of the Venus, both used in the cells, were injected into the fertilized egg C57B16, thereby producing transgenic mice with chromosomes into which each of the constructs has been randomly inserted. In order to detect the expression of Venus in the respective transgenic mice, 13.5-day mouse embryos were recovered, DNA insertion therein was confirmed, and fluorescence was simultaneously observed. The used promoter was the CAGGS promoter which was the same as in the previous experiment, and which is considered to result in uniform gene expression throughout the body.

Figure 7:
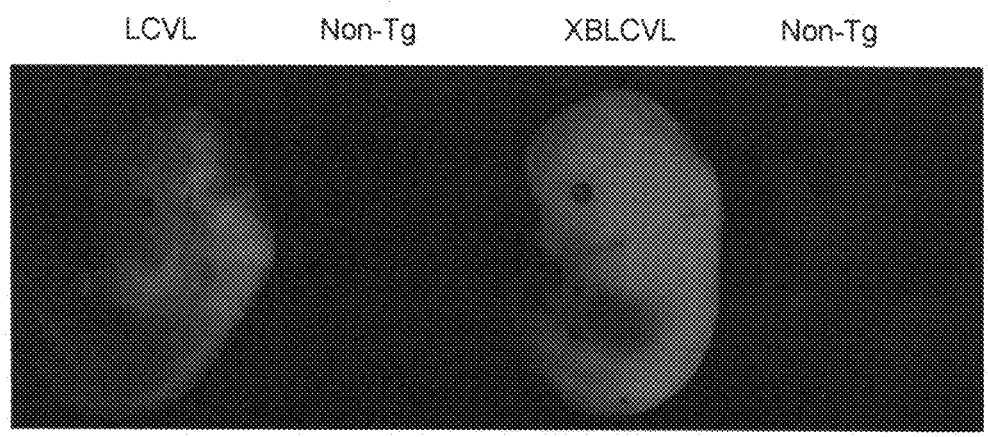
FIG. 7 shows a position effect blocker activity of the XB fragment in the transgenic mice. A. Two mice in left side of the panel, which are mouse fetuses used in experiments for injecting the construct I (indicated as "LCVL") into the egg. The DNA is inserted into mice in the left side, while no foreign DNA is present in the mice in the right side. Two mice in right side of the panel are mouse fetuses used in the injection experiment of the construct II (indicated as "XBLCVL") into the egg. As in construct I, the DNA is inserted into mice in the left side, while the foreign DNA is absent in mice in the right side. B. A table providing the number and percentage (%) of fetuses in which fluorescence could be observed for insertion of DNA in each experiment.

Among the transgenic mice of Construct I, 24 mouse embryos had Construct I, but only two of the 24 embryos expressed fluorescence. Also, one of the two embryos exhibited very weak fluorescence, and the other embryo exhibited a mosaic-like pattern consisting of a site with strong fluorescence and a site with weak fluorescence, as shown in FIG. 7. This indicates that the gene is not uniformly expressed throughout the body. Twelve transgenic mice into which Construct II had been inserted were recovered. Among them, relatively strong fluorescence was observed in 9 mice. As seen in FIG. 7, the fluorescence was observed uniformly in terms of its intensity throughout the body. This indicates that the gene was expressed without site-specificity. That is, the inherent properties of the promoter were maintained regardless of the information in the vicinity of the site at which the transgene has been inserted (i.e., the inherent properties were not influenced by either inhibition or activation).

As shown in FIG. 7, it was demonstrated that a transgene could be stably expressed at individual level accordingly.

Industrial Applicability

The present invention enables a transgene introduced into an animal genome to stably express for a long period of time. Thus, the present invention is useful for production of a peptide, polypeptide, or protein encoded by such transgene, genetic therapy of animals, and other applications.

The present invention is advantageous in that the animal cell or animal with a genome into which the transgene has been randomly introduced (see FIG. 6) or has been introduced via homologous recombination (see FIGS. 1 to 4) would be capable of stable expression of such transgene for a long period of time and capable of transmitting such transgene to its offspring. Because of these properties, the transgene-containing animal cell can be used for production of substances such as peptides, polypeptides, and proteins. Also, a vector comprising a transgene carrying a foreign DNA encoding a therapeutically effective protein can be used for genetic therapy.

All publications, patents, and patent applications cited herein are incorporated herein by reference in their entirety.

The invention claimed is:

1. An isolated transformed animal cell comprising, in its genome, a DNA comprising a promoter operably linked to an exogenous DNA, wherein the DNA has been inserted between two identical XhoI-BamHI fragments (XB fragments), wherein the XB fragments comprise a nucleotide sequence selected from the group consisting of SEQ ID NO: 1, SEQ ID NO: 2, SEQ ID NO: 3, and a nucleotide sequence having at least 99% identity to SEQ ID NO: 1, SEQ ID NO: 2, or SEQ ID NO: 3.

2. The isolated transformed animal cell according to claim 1, wherein the animal cell is a differentiated cell.

3. The isolated transformed animal cell according to claim 1, wherein the animal cell is a vertebrate cell.

4. The isolated transformed animal cell according to claim 1, wherein the vertebrate cell is a mammalian cell or avian cell.

5. The isolated transformed animal cell according to claim 1, wherein the exogenous DNA encodes a peptide, polypeptide, or protein.

6. An isolated animal cell transformed with a vector comprising a DNA comprising a promoter operably linked to an exogenous DNA, wherein the DNA has been inserted between two identical XhoI-BamHI fragments (XB fragments), wherein the XB fragments comprise a nucleotide sequence selected from the group consisting of SEQ ID NO: 1, SEQ ID NO: 2, SEQ ID NO: 3, and a nucleotide sequence having at least 99% identity to SEQ ID NO: 1, SEQ ID NO: 2, or SEQ ID NO: 3.

7. The isolated animal cell according to claim 6, which is a vertebrate cell.

* * * * *

SEQUENCE LISTING

<160> NUMBER OF SEQ ID NOS: 9

<210> SEQ ID NO 1
<211> LENGTH: 2549
<212> TYPE: DNA
<213> ORGANISM: Mus musculus

<400> SEQUENCE: 1

```
ctcgagcaca gcaccgccag ctgaatcgga caaactggag aacctcttgc cagcagtagg      60
gctgtggagc cctctttcca tcagaatcat ctcttttctt attctttcca tcatctcagc     120
tttctaaaaa atgtcacagt ggcctggctg tcccgtctta atgatgggct gcgcccaggg     180
ctgattctca ttcagcccca gcaagcggct ctaaatatta ttatctcttt tggagggagg     240
cggaaaaaat tgtgggatgc cagagcgagg gaatgactgg tcaaaatgac ccatacatcc     300
ttccgagtcg gagatgtcat tcatcaaaaa gtagcgcccg ctcgtcatta aggtacgaat     360
gacgccgttc gaataatcat ttattgtaac aggtttataa gcaaataaat acacgctcct     420
gtcagtgggt aatgaaggcg acttcagagc agacaaatag atccaggtag gagacgagaa     480
gacacgaaga gtgaggaaga aggctccggt cctttgcccg ctcccagcca gttctgctcg     540
cccgggggtt tggcctcggg ggtgaaattg acagtctgat taatagagca cgccgcggcg     600
catttccccc ttcatttagg ggcatcatta cgctctcagt ttgctgggtt gccccttagg     660
tcctaatcat gcagcgcctt cctcatttct ccacgaacac agatacgtgt taaataatag     720
ataatgcttt gattttttcca gggtagattc ttgagaagtt tttgttttgt tttgttttgt     780
tttgttttgc cttaacattt acaagctggg ggcgtaaggg gggcgggtaa aggggaggat     840
acaggaagag ttgcgtaaga agacctcgcg cccactcctg tcaggattac ttatctttct     900
gttttaagaa ccaaatatta ataatgagta ttttatttaa caaatagaat tctgagttct     960
ttctctctcc ttacttttc ctctcagtct tgattctccc ctccaacaca cacacacaca    1020
cagagagaga gagagagaga gagagagaga gagagagaga gagagagaga atatatcttg    1080
tagacttttg aaaatgcttt cttgctacgt ggctgaggag gtacacagga cccgtgccgt    1140
gcctccaagt ggaaatcatt acatcttctc ttattttcta ccactgcttg caggctaact    1200
tctgaactcg aagaccttag attttttgtt ttataatcct ctgatggata agcttctcac    1260
cctcgcattc tcccttaggg gaaataaact agactggagg atctgatagt agaaattgac    1320
agctaacttt aaacacaatc atgatttacc gtaccatagc tccccatcac agaacccact    1380
ttttaaaatt gccggctttc tcccacccct ctcaaataga ggaattcgtg gtgaagtaac    1440
tgggttttgg gggtcaaagt ggagggaatg gaatctcctg ctgcctccct tcctttccca    1500 cttgttctt cttccacttc tccatcctcc ccctcctcca ccctaggccc ttacctgtgg    1560
cccccggtgt tcctggtgct gactgggggc acagagagtc tccaaccagc cttgcctctt    1620
ctccttcccg cctgaggctg gaggctgagc ctcttggcga taactttgat agtcataatg    1680
acgccggtgg caaccatttt aaggaagatc aatcttcact caaatgcgct catctcctcc    1740
cgcgcttgcg ccccacccctg cccgactcag atgcgtcgtg ccagtttgcc cgcctgctgc    1800
cccagaagca gagctttgtc cgcactggcg aggtccacgg aagacaggga caggacacag    1860
tggtctagcg cgtgagcttc cgaagcagcc tagagagcct ggcagtcttg atgctggttt    1920
```

-continued

| | |
|---|---|
| tgcatcccgg tcacaggact aactgagacc ctaacccggg ccccctcct tcccgccttg | 1980 |
| agacacaccc agcatattgg ggtgtgttag ggggtaaacc tctgatctaa ttgcccatct | 2040 |
| gtctgttggc gctttctttt taaccttgga cccgttgggg gcgcgtcaag aatgtaaggg | 2100 |
| gaggtgaggt gtgaaatata tttatataca tgtgtataca tatatagtca atgccaaaag | 2160 |
| tttttcacct cttcccctta gcgccaactt atttctacag gcaagcttgc tggaaaaaaa | 2220 |
| aaaaaaaaaa aaaaaaaaaa caatcccacc tctttaaagt tgtaagtgga aaattgcata | 2280 |
| ggctcgcagg cttaggagaa ttgtctggtg ggcgatgacc tccatttgag aatttgaccc | 2340 |
| agcatccacc tttgccctg tcccagtggc tattctaccc tagtggtcat tcagttcctg | 2400 |
| gcacttgcat tgtcctcaag caggattttg gctacctctc ttcgctaatc acacgtccag | 2460 |
| ctctgcgggc gccccaact gcttctcagc caggacgccc agctccaccg gtccaggcag | 2520 |
| tctgggcccc agtgtctctg ggaggatcc | 2549 |

<210> SEQ ID NO 2
<211> LENGTH: 2498
<212> TYPE: DNA
<213> ORGANISM: Homo sapiens

<400> SEQUENCE: 2

| | |
|---|---|
| cagcattgcc agccgagttg gacaaattgg agaatctctt gcccgccgta gggctgtgca | 60 |
| gccctctctc catcagaatc atctcttttc ttattctttc catcatctca gctttcttaa | 120 |
| aaatgtcaca gtggccctgc tgtcccgtcc taatgatagg ctgcgcctag ggctaattct | 180 |
| cattcagccc cagcgaacgc ctctaaatat tattatcgct ttcggaggga ggcggaaaaa | 240 |
| ttgtgggatg ccagagcgag ggaatgactg gtcaaaatga cccatacatc cttccgatcc | 300 |
| cgagatgtca ttcatcaaaa agtagcgccc gctcgtcatt aaggtacgaa tgacgctgtt | 360 |
| cgaataatca tttattgtaa caggtttata agcaaataaa tacaccctcc tgtcagtggg | 420 |
| taatgaaggc agcttcagag cagacaaata gatccaggta ggaggcgaga agagacaagt | 480 |
| gaggaggaag gctccggtcc tttgcccgct ccgagccagt tctgctcgcc cggggggtttg | 540 |
| gcctcggggg tgaaattgac agtctgatta atagagcgcg ccgcggcaca tttccccctt | 600 |
| catttagggg catcattacg ctctcagttt gctaggttgc cccttaggtc ctaatcatgc | 660 |
| agcgccttct tcattttcc ttggacacag atacgtatta aataatagat aatggtttga | 720 |
| ctttccagag taggtcctcg ggaaggtttg gtttttttt ttttttttt tttttttt | 780 |
| accatttaca agctggggc ataagtgggg ggagataagg gggaggatgc aggaagagtt | 840 |
| gcgtaaggag aagaccttgc gcctctccta tctggattac ttatctttcg gatttcggaa | 900 |
| ccaaatatgt attttattta acaaatagga cgccggagtt cttttccctcc ctatttcttc | 960 |
| acctcagcct aaatgctctc ctcccacccc gggagagaga gagagcggaa gagagggaga | 1020 |
| gagggagaga gggagaaagg gagagggaga cggagtgaga gaaagagaga gagagagaga | 1080 |
| gagagaaata gaaatatcct agagttttga aagcgctttc ttgctacgtg gccgcggagg | 1140 |
| tgcattgggc ccgcgcctcc aaacggaaat cattaggtcc tctctgattt ctaacaccg | 1200 |
| tctgcagagt gagatctgaa ctcgaagtcc ccggtttttt acttttataa tcctgctgat | 1260 |
| agaaagcctt ctcgcctacg cattttcctg aggggaaacg aactaggctg gacgatttga | 1320 |
| tagcagaatt cgacagctaa cttaaacac agtggagatt tacagcgcca tacgggcgct | 1380 |
| ccgaatccac gctcacgttg ccagattttc cctcccctcc tcaaatagaa ttatttgcgg | 1440 |
| caaaggcgct ggatttcgag gtcaaaagag gaaagaggag acagccttct tcccctacct | 1500 |

```
ccccgctgcc ctcccttccc ctttgctttt cttccttctc tctttcctcc cctcatcaac    1560
cccagcccct tacctgcggc cacaggtatt cccagcgttg ggtccgggcg cagagagtcg    1620
ccgaacagcc ttacagcagc tctctgcggc ctgggcttgg aggctgagcc tcttggcgac    1680
aactttgata gtcataatga cgccggtggc aaccatttta acgaagatca atcttcactc    1740
caggccgctc ctcatctccc gcggttgcgc ccaccttcc ctgaccctcc aagcactgtg     1800
cccacccgcc aacggcccag ccggagagag attcgcggac acaggcggag gcagggagg     1860 acggggatgg gacgcggagg tccgcccgtg agcttctgaa gcggctgaga gaccctgaca    1920
atctgggcgc tgggcgcggg tcctgcatcc ccacatttag cctcaatccg aaccccaacc    1980
agggccccct cttctttctg ccgacacacc cagaacattg gggtgtgtta ggggcaagc     2040 tcgagatcta ttcgcctata gctcttggcg cttttccttt aaccttagac ccgttggggg    2100
cgcatcagga atgtaagggg aagcgaggtg tgaagtatat ttatatacat atatacacac    2160
atatagtcaa tgccaaaagt ttatcttctg ttcccctcgg cgccaactta tttcaacaac    2220
gcgagctttg cttagaaaat caattccaca tctttaaggt aataaacgga aagctcgata    2280
ggcaggcggt gcctggggga acggggaacc ggcggggaac gcagagtggg catccagcgc    2340
accgggactg ggacttgacc cagcgtccac ctctgccct gccccattgg ccacccagct     2400
ccgagctccc tgagttctca ttgcgccggc tttggggcca tcagcgcggt gggagtccag    2460
ccctgccaac gcccccacct gctccctccc tgctccgc                            2498

<210> SEQ ID NO 3
<211> LENGTH: 2600
<212> TYPE: DNA
<213> ORGANISM: Gallus gallus
<220> FEATURE:
<221> NAME/KEY: modified_base
<222> LOCATION: (1196)..(1434)
<223> OTHER INFORMATION: a, c, t or g
<220> FEATURE:
<221> NAME/KEY: modified_base
<222> LOCATION: (1488)..(1488)
<223> OTHER INFORMATION: a, c, t or g

<400> SEQUENCE: 3
ctccagcacc gcatttccag ctgagtctga caaattcgag agccttttgc cagccgtagg      60
gctgtgcagc cctctctcca tcaggatcat ctcttttctt attctttcca tcatctcagc    120
tttataaaaa atgtcaaagt tgcagggctg gtcccgtact aatgatgagc tgcggcaggg    180
gctaattcac attcagcccg gagagcgtct ctaaatatta ttatctcttt ttgagggagg    240
cgtaaaaact gtgggatgcc aaagcgaggg aatgactggt caaaatgacc catacatcct    300
tcctagcccg aaatgtcatt catcaaaaag tagcgctcgt cattaaggta cgaatgacgc    360
cgttcgaata atcatttatt gtaacaggtt tataagcaaa taaatacaag ctcctgtcag    420
tggataatga aggcggcttc tgagcagaca aatatatcca ggtggaaaga aagagagacg    480
agaagtgagg agcaaagctc tcgtcctcag cttgatcaga tcctgcttga attgctctgg    540
ggtttggcct ctggggtgaa attgacagtc tgattaataa aatgagctgt gcaacatttc    600
ccccttcatt taggtgcatc attatgctct gattttgtt ttgttgcctt ttaggtccta     660
atgatgcagc ttcttttctca tttgtcctcg acagaacca cacgctaaat gttagataac    720
gcttttcttt attattagct gggaggcgga ttggatcgcg acgcgcggag ccgccggcac    780
gagagcggcg gggagagcat ctccgccgct gacacctcgt tactttttccс tcccatcttc   840
```

```
cgaccgcgtt cgtactttta tagaggcatt tctgcggcac ccccgtgcac ccctcacac      900 cccgagccct gcgctggac ttgacgtgcc cgctgcacgc cgcgcttcgg gcgcacctcc      960
agcagccgcc cgcaaattga acagcggtt agcatccctg cttcccgatg catctcttcg     1020
ttgcgtcctt acacgcggta ttctttctac ttcccgtaac cgttcgccgg cgaagctgcc    1080
ctatgggaca acgttcgctc tgatagcagg gagaagagct cgaagggtac gaaacgcagc    1140
cgcgtgggca gcgggctcct ctctccagcc cttcttccct cccccgccc atttcnnnn      1200 nnnnnnnnnn nnnnnnnnnn nnnnnnnnnn nnnnnnnnnn nnnnnnnnnn nnnnnnnnnn    1260
nnnnnnnnnn nnnnnnnnnn nnnnnnnnnn nnnnnnnnnn nnnnnnnnnn nnnnnnnnnn    1320
nnnnnnnnnn nnnnnnnnnn nnnnnnnnnn nnnnnnnnnn nnnnnnnnnn nnnnnnnnnn    1380
nnnnnnnnnn nnnnnnnnnn nnnnnnnnnn nnnnnnnnnn nnnnnnnnnn nnnncttct    1440 catttttctc cccccaaaca acagcacaac gtaagccgat tagggctntt caccgaaatg    1500
aacgggcgaa cgaggagcct gttgcagaga gcggcaaaat agacgaagtt tactcagttg    1560
ctcctatgat tttaaagatc tgctcaggcc cgtttccaaa cttttattt ttaccttgaa     1620 agttattacc gcaggcatca aagaatattt tcggtacact tttattaaat cttagccctg    1680
gagaaaacat gagggcactc catttaattg gaacgcggct cgcagcgagc cagccgctcc    1740
cagggccaga aggacagcgg ggctgccggc tccccttct gccgcacggc tccgcggccg    1800
cgcaacgtct ccgcgcagcg cagagccggg cagcgcgggg cgctcggagc gcggagcccc    1860
gcgcggtgcc cgcggcgggc ggcgacaggc gcggcgcgcg ccacctggcg gctctgcgcg    1920
gctttgcgcg ctcgctgcgc ggggcggagg ctgcgcgctg ccctgggccg ccgccgtccg    1980
cctcggtgcg ccgcgttccg cccggctctg ccccgccgc acgccggccc gtagggaagg    2040
tcggggcgct gcgacgcgt cggtccgtgc ttcgaagcgg aaagagctgc ggcgcgtccc    2100
cgggtcacgc ggggccttcg gcacggtcgc gccccgaggc acgcgggctg cggtccggcg    2160
gcgtccggtt gtgcgatcgt ttttggggct ggcctccgtt taggcaataa aacgggctc    2220 cgtccgaaaa gccgccgggc gggtgtttat gttcagcccg gagcgctcgt ccgggccggg    2280
acgccgcggt tcccgttgcg cttcggggta cgcaggggcc ggagcggctg cgctcacccg    2340
acggatcgag ggcagcttct gagagagatc cgagggaact tctccgccct cagaacggat    2400
tgtttgttta acgttgaaat aaagaaaggg atgagagtac atgaacgaaa aaaaaaatgg    2460
gagtaacaaa agagatgagt gtacagaaag agacggggt aactaaggag atgagggtac     2520
ttaatgagaa gagggtacat aaagagatgg gactcaatac agagacgaga tgctacggtg    2580
caggtttgga gattaaaaac                                                2600
```

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catgtttgag accttcaaca c                                                21

<210> SEQ ID NO 5
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 5
gtgatgacct ggccgtcagg                                               20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtgtccagt tgtggctgat c                                             21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctaccacgca ttccctgtct g                                             21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtttcccgg tggagaagta c                                             21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tggacaccat gtcgatgtag c                                             21
```